United States Patent [19]

Deutsch et al.

[11] Patent Number: 4,935,222
[45] Date of Patent: Jun. 19, 1990

[54] PROCEDURE FOR ISOLATING AND PURIFYING RADIOACTIVE LIGATED RHENIUM PHARMACEUTICALS AND USE THEREOF AND KIT

[75] Inventors: Edward A. Deutsch, Cincinnati; Harry R. Maxon, III, Terrace Park; Karen F. Libson, Cincinnati, all of Ohio; Alan R. Ketring, St. Charles, Mo.

[73] Assignee: University of Cincinnati, Cincinnati, Ohio

[21] Appl. No.: 873,990

[22] Filed: Jun. 13, 1986

[51] Int. Cl.$^5$ .................... A61K 49/02; C01G 47/00
[52] U.S. Cl. .......................................... 424/1.1; 423/2
[58] Field of Search ............................. 424/1.1; 423/2

[56] References Cited
U.S. PATENT DOCUMENTS

| | | |
|---|---|---|
| 3,733,388 | 5/1973 | Ziegler . |
| 4,123,497 | 10/1978 | Ruddock . |
| 4,185,078 | 1/1980 | Quatrini et al. . |
| 4,387,087 | 6/1983 | Deutsch et al. . |
| 4,401,646 | 8/1983 | Rhodes et al. . |
| 4,440,738 | 4/1984 | Fawzi et al. . |
| 4,512,967 | 4/1985 | Linder . |
| 4,707,544 | 11/1987 | Jones et al. .......................... 424/1.1 |

OTHER PUBLICATIONS

R. P. Spencer, M.D., Ph. D., "Therapy in Nuclear Medicine", 1978, pp. 257-260.

M. Eisenhut, "Iodine-131-Labeled Diphosphonates for the Palliative Treatment of Bone Metastases: 1, Organ Distribution and Kinetics of 1-131 BDP3 in Rats", The Journal of Nuclear Medicine 25:1356-1361, 1984.

Eisenhut, M., Preparation of $^{186}$Re-Perrhenate for Nuclear Medical Purposes, International Journal of Applied Radiation and Isotopes, vol. 33, pp. 99-103, (1982).

Mathieu, L. et al., Preparation of Rhenium-186 Labelled EHDP and its Possible Use in the Treatment of Osseous Neoplasms, International Journal of Applied Radiation and Isotopes, vol. 30, pp. 725-727, (1979).

Weininger, J., A. R. Ketring, E. A. Deutsch, $^{186}$Re--HEDP: A Potential Therapeutic Bone Agent, From the Chemistry Dept. of Univ. of Cincinnati, Nuklearmedizin 2 (1984).

Potsaid, M. S. et al., [32P] Diphosphonate Dose Determination In Patients with Bone Metastases from Prostatic Carcinoma, J. Nucl. Med. 19:98-104, 1978.

Primary Examiner—John S. Maples
Attorney, Agent, or Firm—Wood, Herron & Evans

[57] ABSTRACT

A sterile pyrogen free $Re^{186}$ or $Re^{188}$ radiopharmaceutical is prepared by reducing radioactive perrhenate in the presence of a bone seeking ligand to form a solution including complexed Re-ligand compound together with impurities such as uncomplexed perrhenate, $ReO_2$ and free ligand. The radiopharmaceutical is obtained by a low pressure purification method. The solution is added to a separation column, preferably an ion exchange column, and a first portion is eluted and discarded. The radiopharmaceutical is collected in a second eluted portion defined as having 25-85% of the activity of the Re on the column, less than 10% unligated perrhenate and less than 1% $ReO_2$. This can be used as is to image and treat metastatic bone leasions. A simple kit is also disclosed.

15 Claims, 2 Drawing Sheets

PROCEDURE FOR ISOLATING AND PURIFYING RADIOACTIVE LIGATED RHENIUM PHARMACEUTICALS AND USE THEREOF AND KIT

The research leading to this invention was funded by a grant received from the National Institute of Health. The U.S. Government is hereby granted a nontransferable irrevocable nonexclusive license to practice or have practiced on behalf of the U.S. the invention claimed herein.

BACKGROUND

Radioactive compositions and complexes have found increasing diagnostic and therapeutic applications. For diagnostic purposes, radioactive complexes have been used to provide both negative and positive images of body organs, skeletal images and the like. 99m-Tc-diphosphonate radiopharmaceuticals have been used for some time to image skeletal lesions, including metastatic cancer to bone. Imaging agents typically employ low energy gamma emitting isotopes which, while useful diagnostically, have little therapeutic effect.

Beta emitting isotopes have been used in the treatment of certain cancers but are not useful for diagnostic imaging. To be effective, these beta emitting radiopharmaceuticals must localize in the cancerous lesion and not be widely distributed throughout the body. For example, if a bone seeking therapeutic radiopharmaceutical fails to localize in the metastatic bone lesion, it will either provide no beneficial treatment or require such a high dose as to damage nondiseased tissues and organs.

Various pharmaceuticals have been proposed as therapeutic agents. For example, in the Journal Of Nuclear Medicine, Volume 19, number 1, page 98 (1978), it was proposed to use 32-P labelled diphosphonate to treat patients with bone metastases from prostatic carcinoma. The diphosphonates are useful since they are known to localize preferentially in bone and even more preferentially in or around the metastatic cancer tissue. Further, Mathieu et al in the International Journal of Applied Radiation and Isotopes, volume 30, pp. 725–720 (1979), showed uptake in rat models and suggested the use of a rhenium-186 labelled diphosphonate HEDP (HEDP=1-hydroxyethylidene diphosphonate) for the treatment of osseous neoplasms. A similar diphosphonate complex is disclosed in the International Journal of Applied Radiation and Isotopes, volume 33, pp. 99–103 (1982).

The rhenium complexes disclosed in these references are of little clinical value as radiopharmaceuticals because the disclosed complexes are impure mixtures of complexed rhenium, uncomplexed perrhenate, rhenium dioxide and many other as yet unidentified species. Failure to isolate the active components of these mixtures prevented appreciation that portions of these mixtures would in fact preferentially localize in or around metastatic tissue and provide radiation treatment.

Subsequent studies have demonstrated the separation of 186-Re-diphosphonate mixtures into component complexes using high performance liquid chromatography (HPLC). Further, it was shown that the HPLC isolated 186-Re-diphosphonate complexes would localize in bone lesions. See for example Nuklearmedizin 23: 81-2, (1984).

This academic study, although interesting in that it provides proof that the HPLC isolated rhenium diphosphonate complex does in fact localize in bone lesions, fails to provide a practical treatment method which can be widely used. Typical radiopharmacies simply do not have the capabilities of routinely performing complicated procedures such as high performance liquid chromatography.

These studies demonstrated that isolated rhenium complexes can localize in metastatic bone tissue but that impurities formed in the manufacture of the ligated rhenium reaction mixture prevent successful use of the unpurified reaction mixture. The known separation techniques for isolating the ligated rhenium complex are simply too complicated for routine use in a radiopharmacy.

SUMMARY OF THE INVENTION

The present invention is premised on the realization that a sterile, apyrogenic radiopharmaceutical can be provided by first forming an unpurified mixture of ligated rhenium which would typically include uncomplexed perrhenate, unreacted ligand, rhenium dioxide as well as other unidentified impurities. This impure mixture is then sorbed onto an appropriate separation media such as an ion exchange resin in a low pressure or gravity flow column. A first portion of impurities is eluted with an appropriate eluent, which, for example, in ion exchange chromatography would be an aqueous solution having a low molar ion concentration. A second portion is eluted with an appropriate eluent, which, for example, in ion exchange chromatography would be an aqueous solution having a higher ion concentration. A third portion of impurities is left uneluted on the chromatographic resin. The useful radiopharmaceutical is collected generally from the second fraction. Specifically, the radiopharmaceutical will be a fraction containing 20–85%, but most usefully 30–70%, of the activity of the radioisotope on the column. This activity should contain less than 10% unligated perrhenate and less than 1% of rhenium dioxide.

In a preferred embodiment, the pharmaceutical is a bone localizing agent formed by ligation of a polydentate phosporous containing ligand to the radionuclide. Preferably, the radionuclide is 188-Re or 186-Re. The present invention, as well as its advantages, will be further appreciated in light of the following detailed description.

DETAILED DESCRIPTION

Figure 1:
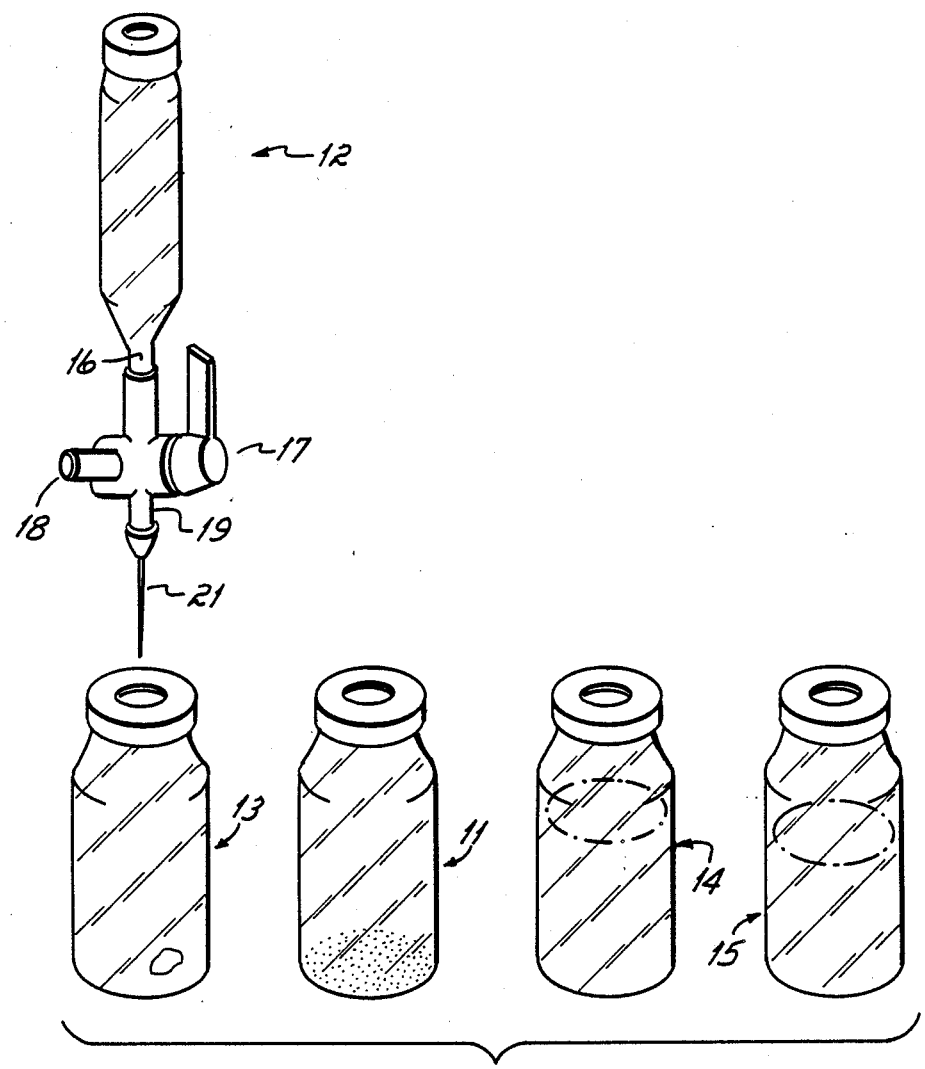
FIG. 1 exploded view of a kit for use in the present invention.

According to the present invention, a pharmaceutical including complexed rhenium is obtained from a crude mixture which in addition to the complexed rhenium includes rhenium dioxide, unligated perrhenate, excess ligand, and many complex, undefined compounds.

Radioactive perrhenate is formed by various methods. Rhenium-186 is formed by irradiating rhenium metal (rhenium-185) with a strong neutron radiation. Typically a radiation having a flux of 1014 neutrons $cm^{-2}s^{-1}$ will form rhenium-186. This is well known in the art.

The rhenium-186 metal is oxidized by a strong oxidant such as hydrogen peroxide, nitric acid, and the like. This forms a solution of perrhenate ($ReO^-_4$). This solution is then neutralized with a strong base such as ammonia or a strong acid such as hydrochloric acid or sulfuric acid as required. The formed solution includes perrhenate-186 together with the bi-products of the oxidation of the rhenium metal along with the salts generated by the neutralization.

An aqueous crude solution of perrhenate-188 can be formed in this same manner with the exception that the rhenium starting material would be rhenium-187 as opposed to rhenium-185. More preferably, a crude aqueous solution of perrhenate-188 is formed by simply eluting a tungsten-188/rhenium-188 generator with, for example, saline solution.

The obtained perrhenate can be used as is or further purified. To purify the perrhenate the crude aqueous solution of the radionuclide is treated with a lipophilic counter cation. The lipophilic cation must be one which is at least slightly soluble in water so that it can go into solution with the perrhenate. An example of such would be tetraethyl ammonium, tetraethyl arsonium, tetraethyl phosphonium, tetrabutyl ammonium, tetrabutyl phosphonium, tetrabutyl arsonium, tetrapropyl ammonium, tetrapropyl arsonium, tetrapropyl phosphonium, tetraphenyl arsonium, tetraphenyl phosphonium, tetracyclohexyl phosphonium, tetracyclohexyl arsonium, trimethyl ammonium, dibutyl diethyl ammonium, tributyl ethyl ammonium, triethyl sulfonium, and so forth. These are generally salts, such as halides, particularly chloride.

The associated perrhenate is formed by simply adding the lipophilic counter ion to the crude aqueous mixture containing the radioactive perrhenate. The perrhenate associated with the lipophlic counter ion is then separated from the aqueous mixture by preferential sorption. More specifically, the solution is added to a reverse phase separation medium and the aqueous components are removed with water. The radioactive perrhenate can then be removed in ethanol. This is disclosed in the application of Deutsch et al, Serial Number 802,779, now U.S. Pat. No. 4,778,672 entitled "METHOD OF ISOLATING RADIOACTIVE PERRHENATE OR PERTECHNETATE FROM AN AQUEOUS SOLUTION", filed Nov. 27, 1985, the disclosure of which is incorporated herein by reference.

Rhenium-186 radiopharmaceuticals contain significant amounts of carrier rhenium. Thus, the total concentration of rhenium present during the preparation of rhenium-186 radiopharmaceutical is on the order of $10^{-3}$ M. When a W-188/Re-188 generator is used to generate rhenium-188, the total concentration of rhenium present during preparation of rhenium-188 radiopharmaceutical is on the order of $10^{-8}-10^{-6}$ M.

The obtained perrhenate is then ligated to a bone seeking ligand. Bone seeking ligands include mono-, bi- and polydentate ligands. Specifically included ligands are the poly- and pyrophosphates, the phosphonates, phosphonites, and imidodiphosphates. The preferred ligands are the diphosphonates which have the following general formula:

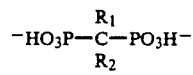

and pharmaceutically acceptable salts thereof.

Specific ligands include the diphosphonates wherein $R_1$ and $R_2$ represent the following:

|  |  | Abbreviated Name |
|---|---|---|
| $R_1$=OH | $R_2$=$CH_3$ | HEDP |
| $R_1$=OH | $R_2$=H | HMDP |
| $R_1$=H | $R_2$=H | MDP |
| $R_1$=H | $R_2$ = CH—COOH<br>      \|<br>      $CH_2$—COOH | DPD |
| $R_1$=H | $R_2$=$N(CH_3)_2$ | DMAD |
| $R_1$=H | $R_2$=$CH_2CH_2NH_2$ | AEDP |
| $R_1$=OH | $R_2$=$CH_2CH_2NH_2$ | APD |

Also suitable are the monophosphonates such as

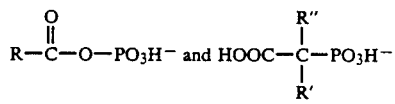

and pharmacologically acceptable salts thereof where R' is generally $NH_2$ or $C_1$-$C_{10}$ alkyl while R' and R" are generally H or $C_1$-$C_{10}$ alkyl. Analogous arsonate ligands are also suitable.

The counterion associated with these ligands are generally alkali metals such as $Na^+$ as well as any other pharmaceutically acceptable counterion. These of course are well known and, per se, form no part of the present invention.

A discussion of bone seeking ligands is contained in Radiopharmaceuticals: Progress and Clinical Perspectives, Volume II, pp. 128-140 (1986).

The radioactive perrhenate is then reduced and complexed with the selected ligand. Specifically, the aqueous solution of perrhenate is combined with the ligand and a reducing agent and, optionally, a buffer and/or an antioxidant such as ascorbic acid, gentisic acid or p-aminobenzoic acid. The complexation reaction is conducted by simultaneously reducing the perrhenate in the presence of the selected ligand. Suitable reducing agents include stannous chloride, sodium borohydryde, sodium dithionite, tin metal and formamidine sulfinic acid. The formed complex is designated by a name which includes the reducing agent and the ligand, for example, 186-Re(Sn)HEDP, 188-Re($NaBH_4$)MDP, etc.

The preparation of the radioactive imaging agent will better be appreciated in light of the detailed description of the formation of 186-Re(Sn)HEDP.

EXAMPLE 1

To form 186-Re(Sn)HEDP, 186-perrhenate (186-$ReO_4^-$) is reduced by stannous ion in the presence of the HEDP ligand. A typical preparation contains 0.5 mg Re (with 75-100 mCi 186-Re), 25-30 mg $SnCl_2.2H_2O$, 75 mg $Na_2H_2HEDP$ which prevents the precipitation of stannous salts at neutral pH and 10 mg ascorbic acid as an antioxidant. The pH of this mixture is optimally 3.0-3.5 for HEDP, although this value will be different for other ligands. These reagents can be provided in a sterile, lyophilized kit as is standard practice in the art. An aqueous solution of perrhenate is combined with the tin-HEDP mixture and the reaction mixture is either heated or allowed to incubate for several hours. Typically, for 186-Re (Sn) HEDP, the reaction is heated at 90–100° C. for 10 minutes.

To determine the degree of complexation, a paper chromatography method can be used. Strips of Whatman 3mm paper which are 10 centimeters long and approximately 1.5cm wide are used. With a pencil, 3 lines are drawn across the strips at 1.5cm, 3.0cm, and 7.0cm. Two of these strips are spotted with a small drop (1–5 microliters) of the 186-Re(Sn)HEDP preparation at the 1.5cm mark. One strip is eluted with acetone the other with 0.15 molar NaCl. When the solvent reaches the top of the strip, they are removed, allowed to dry and then cut at the 3 cm and the 3cm marks. Each section of the two strips is counted in a NaI well detector. The counts are used to determine the complexation yield as follows:

$$\% \ ReO_4^- = \frac{\text{counts in top section of acetone strip} \times 100}{\text{sum of all three sections of acetone strip}}$$

$$\% \ ReO_2 = \frac{\text{counts in bottom section of NaCl strip} \times 100}{\text{sum of all three sections of NaCl strip}}$$

% Complexation = 100 − % $ReO_4^-$ − % $ReO_2$ (should be >90%)

After the incubation, the complex mixture of components comprising 186-Re(Sn)HEDP is purified by a low pressure or gravity flow chromatographic procedure using an appropriate separation medium.

Low pressure is intended to distinguish over HPLC which operates at extremely high pressures generally at 500 to 4000 psi. Low pressure refers to pressures generally less than 40 psi and preferably simply a gravity flow column. Such low pressure columns are considered substantially less effective than HPLC but are low cost and easy to use and easy to maintain sterile and pyrogen free. Therefore low pressure columns, when effective, are clinically useful whereas HPLC is generally not clinically useful.

Suitable separation media would include ion exchange resins, ion exchange membranes, size exclusion media, metal oxides such as alumina or silica, reverse phase substrates, and the like. Particularly useful separation media include Cellex DEAE, Cellex QAE, Sephadex QAE, IsoRx 20, Sephadex DEAE, Dowex AG-1-MP, Dowex AG-1 and QMA as provided in the Waters Assoc. Sep. Pak Cartridge.

The separation medium is prepared as recommended by the manufacturer, usually by storing in sterile water for 24 hours and then washing several times with sterile water. The prepared medium is then used to generate a column using techniques familiar to those skilled in the art. This column can be prepared in a sterile, apyrogenic fashion suitable for shipping and radiopharmaceutical preparation (FIG. 1).

The prepared column is loaded with the crude 186-Re(Sn)HEDP mixture. If an ion exchange medium such as Cellex DEAE is used, the crude mixture is diluted before loading with $3 \times 10^{-3}$M ascorbic acid solution to achieve a sufficiently low ionic strength to allow adsorption to the ion exchange medium. The loaded ion exchange column is initially eluted with an aqueous solution of low ionic strength. Preferably the ionic strength of the aqueous solution will be in the order of $(1-10) \times 10^{-3}$ molar. For 186-Re(Sn)HEDP, this solution is $(1-5) \times 10^{-3}$ M ascorbic acid. About three column volumes of this first eluant should be passed through the column to remove impurities.

The ion exchange column is next eluted with an aqueous solution of a higher ionic strength. Preferably the higher ionic strength solution will comprise a pharmaceutically acceptable solution such as, for example, normal saline, 0.10–0.15 molar sodium phosphates, 0.15 molar sodium acetate, etc. Generally the higher ionic strength solution should have an ion concentration in the range of 0.10 to about 0.30 molar. To provide for stability of the eluted composition, the eluant preferably includes a small quantity of ascorbic acid as an antioxidant and of ligand to assist in stabilization of the eluted product. The pH of the eluant must also be maintained in order to provide a pharmaceutically acceptable agent and to prevent any additional reactions. The pH may be in the range 4–9, but is most usefully maintained in the range 5–8, the exact value depending on the ligand and chromatographic procedure being used. For 186-Re (Sn) HEDP, a suitable eluant is 0.9% NaCl containing 0.01 M $Na_2$ HEDP and $3 \times 10^{-3}$ M ascorbic acid, at pH 5.0.

Generally 25–85% and preferably 30–70% of the total rhenium radioactivity is eluted from the column. This radioactivity can be collected in individual fractions, the fraction with the highest specific activity and chemical purity being used as the radiopharmaceutical. Generally, the final radiopharmaceutical will have a specific activity of about 10–30 mCi/ml, and a total volume of 5–10 ml. This radiopharmaceutical is then filtered through a 0.22 micron sterile filter, preferably one made from an inert material such as Teflon, for example, the 0.22 micron Millex FG or Fluoropore provided by Millipore Corp. After conducting the appropriate quality control procedures to determine % $ReO^-_4$ and %$ReO_2$, the desired fraction is injected directly into the individual being treated.

The use of this application will be further appreciated in light of the following detailed description of the preparation of 186-Re (Sn) DMAD.

EXAMPLE 2

In a serum vial containing 2 ml water are dissolved 10 mg ascorbic acid, 25 mg $SnCl_2 \cdot 2H_2O$ and 75 mg DMAD, the pH being in the range 1–2. (These reagents can also be provided in a sterile, apyrogenic, lyophilized kit as is standard practice in the art). To this reagent solution is added 186-$ReO_4^-$, and the resulting mixture is heated at 90–100° C. for 10 minutes. This reaction mixture is assayed for $ReO_4$ and $ReO_2$. The diluted reaction mixture is added to a Cellex DEAE column, and the column is then flushed with three column volumes of $3 \times 10^{-3}$ M ascorbic acid (pH 2.2) to remove impurities. The desired radiopharmaceutical is then eluted with 0.9% NaCl containing 0.01 M DMAD and $3 \times 10^{-3}$ M ascorbic acid, at pH 2.2. This solution is brought to pH 5–7 by addition of a sterile solution of NaOH, and is filtered through a 0.22 micron filter as described above.

Figure 2:
FIG. 2 is an image of a rat obtained with the radiopharmaceutical of the present invention.
Figure 3:
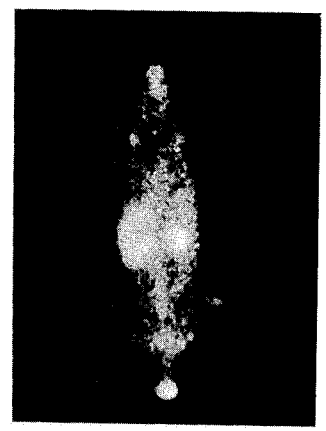
FIG. 3 is an image of a rat obtained using unpurified radiopharmaceutical.

To demonstrate the quality of the obtained radiopharmaceutical, FIG. 1 is presented which shows the image obtained when a rat is injected with a radiopharmaceutical obtained according to Example 1. FIG. 2 is a comparative image obtained when the radiopharmaceutical is not purified according to the method of the present invention and is obtained essentially according to the same method shown or described in the Mathieu article Preparation of Rhenium-186 Labelled HEDP and Its Possible Use in the Treatment of Osseous Neoplasms.

Thus according to the method of the present invention, a radiopharmaceutical can be obtained very quickly and easily and is shown to perform substantially as well as a radiopharmaceutical obtained through a high performance liquid chromatography or other highly technical and difficult separation techniques. However, the method of the present invention is particularly suitable for use in a radiopharmaceutical laboratory and does not require a high degree of technical ability to perform a useful separation.

The present invention is particularly suitable for use in the preparation of a kit for use by radiopharmaceutical laboratories. The kit would preferably include a vial 11 of a lyophilized mixture of the reductant, for example, 25 mg stannous chloride, the ligand, for example, 75 mg HEDP and an antioxidant. Further, the kit should include a separation column 12, a collection vessel 13, a second vial containing a first eluant 14, and a third vial containing a second eluant 15. The separation column could be packed with the separation medium and ready to use enclosed in a sterile, pyrogen free package.

As shown in FIG. 1, the column is stoppered and sealed with a crimped metal seal to maintain sterility. Likewise vial 11 is stoppered and sealed. Rhenium-186 (usually 0.5 mg rhenium containing 75–100 mCi perrhenate-186) in 1 ml absolute ethanol is obtained from the previously described purification procedure. Vial 11, containing the stannous chloride and ligand, is reconstituted with 2 ml sterile water.

The rhenium-186 is injected into vial 11 and the resulting mixture is either heated for about 10–15 minutes in an oil bath at 90–100° C., or is allowed to stand at room temperature for several hours depending on the ligand and the reaction pH. This reaction mixture is then added onto a top of the sterile separation column 12. The column 12 is packed with, for example, Cellex DEAE and is equipped with an exit port 16 which can connect to a three-way valve 17. The dimensions of a typical column are 1.5 cm. I.D.×2.0 cm.

In the first position, the three-way valve 17 allows for the discharge through side port 18 of any unwanted material. In the second position, it allows discharge of the material through bottom port 19 into collection vessel 13. Preferably the second discharge opening 19 would extend through a hypodermic needle 21 which would permit the desired fraction to be collected directly into the collection vessel 13 which is preferably an evacuated vial. This vial 13 can also include a small piece of tin metal to stabilize the collected radiopharmaceutical.

About 10 ml of the first sterile eluant, generally $3 \times 10^{-3}$ molar ascorbic acid would be allowed to run through the column and drained out of the discharge port. About 10 mls of the second eluant then would be taken from vial 15 and added to the top of the column. The second eluant preferably is normal saline in combination with $3 \times 10^{-3}$ M ascorbic acid and $1 \times 10^{-3}$ M ligand. About 1 ml of this second eluant is drained through the discharge port and then 3–5 mls are collected through the collection port into the evacuated vial. This material can then be filtered and directly injected into a patient for diagnosis and treatment. The kit may also include an appropriate filter preferably a 0.22 micron Teflon filter.

The advantage of this kit is its simplicity and effectiveness. It is simple enough to permit radiopharmacies to conduct the preparation without elaborate equipment. Even without the elaborate separation equipment, an effective radiopharmaceutical which can be used without further preparation or purification is obtained.

The invention will be further appreciated in light of the following clinical example which compares the radiopharmaceutical of the present invention with $^{99m}Tc$ (Sn) MDP used to image an individual with diagnosed metastatic lesions. $^{99m}Tc$ (Sn) MDP is the standard diagnostic bone imaging agent used in clinics.

CLINICAL EXAMPLE

Figure 5:
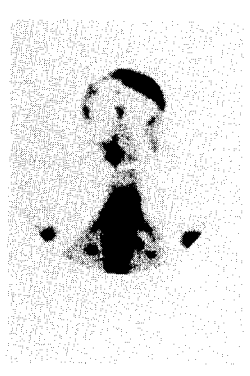
FIG. 5 is an image of an anterior of a human skull obtained using $^{99m}$Tc (Sn) MDP, a standard diagnostic bone imaging agent.

A man age 71 with cancer of the prostrate which had spread to bone was injected with 24 mCi of $^{99m}Tc$ (Sn) MDP. Three hours after intravascular injection, the patient's bones were imaged for metastatic lesions using a gamma camera. The image obtained is shown in FIG. 5.

Figure 4:
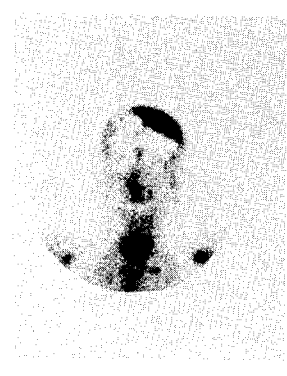
FIG. 4 is an image of an anterior view of a human skull obtained using the radiopharmaceutical of the present invention.

Four days later, the same patient was injected with 4.9 mCi of the $^{186}Re$ (Sn) HEDP compound made according to method described in Example 1. After a period of three hours, the patient was imaged again using a gamma camera. The image obtained is shown in FIG. 4. Blood and urine clearance evaluations were made over 72 hours post injection of the 186 Re (Sn) HEDP and indicated a very rapid clearance from the blood (with less than 6% remaining after 3 hours) with 57% of the material excreted into urine by 22 hours. The test indicated no abnormal rise or change in blood pressure or heart rate after injection and no change in the patient's blood count or blood chemistry tests. As can be seen, the image obtained with the 186Re (Sn) HEDP, is substantially the same as that obtained using the gamma emitting $^{99m}Tc$ MDP. This is very important because the Re complex is also a beta emitter and therefore provides a therapeutic modality which is directly related to the diagnostic information obtained with the gamma camera. Thus, the obtained image provides an accurate indication of the applied radiation dose. Generally for diagnostic application up to 15–20 mCi of $^{186}Re$ (Sn) HEDP may be used.

For therapeutic use, generally a dosage which would subject the bone marrow to less than 100 rads is used in order to prevent irreversible destruction of the bone marrow. However, in severe cases, larger dosages could be used to treat metastatic lesions while sacrificing existing bone marrow. Generally, a dosage providing a bone marrow radiation of less than 100 rads is preferred. Depending on the individual, this might require much larger administered activities and intervenous injections of up to several hundred mCi of $^{186}Re$ (Sn) HDEP. This treatment can be repeated after a period of several months if the patients blood counts are adequate.

Thus, having described our invention, we claim:

1. A sterile pyrogen-free radioactive pharmaceutical formed from a complex aqueous mixture, said aqueous mixture formed by reacting radioactive perrhenate with a ligand under reducing conditions thereby causing at least a portion of said perrhenate to bond to said ligand forming rhenium ligated to said ligand, said ligand selected from the group consisting of polyphosphate ligands, pyrophosphate ligands, phosphonate ligands, diphosphonate ligands, imidodiphosphate ligands, polyphosphonate ligands and arsonate ligands;

adding said complex aqueous mixture to a separation medium, eluting at low pressure an undesirable first portion of said mixture with an eluent to remove impurities; and eluting a second portion from said mixture with a pharmaceutically acceptable eluent and collecting that fraction of said second portion having from 20–85% of the radioactivity of the rhenium on said separation medium and further having less than 10% unligated perrhenate and less than 1% $ReO_2$ wherein said second portion is said sterile pyrogen free radioactive pharmaceutical.

2. A method of diagnosing and treating metastatic bone lesions in a human comprising injecting an effective amount of the radiopharmaceutical claimed in claim 1 into said human.

3. The radioactive pharmaceutical claimed in claim 1 wherein said rhenium is rhenium 188.

4. A method of diagnosing and treating metastatic bone lesions in a human comprising injecting an effective amount of the radiopharmaceutical in claim 3 into said human.

5. The radioactive pharmaceutical claimed in claim 1 wherein said rhenium 186.

6. A method of diagnosing and treating metastatic bone lesions in a human comprising injecting an effective amount of the radiopharmaceutical claimed in claim 5 into said human.

7. The radioactive pharmaceutical claimed in claim 1 wherein said separation medium is an ion exchange medium and said first eluent has an ionic strength less than $1 \times 10^{-3}$M and said pharmaceutically acceptable eluent has an ionic strength of at least about 0.1M.

8. A method of diagnosing and treating metastatic bone lesions in a human comprising injecting an effective amount of the radiopharmaceutical claimed in claim 7 into said human.

9. The radioactive pharmaceutical claimed in claim 7 wherein said pharmaceutically acceptable eluent is selected from the group consisting of saline, an aqueous solution of sodium phosphate and an aqueous solution of sodium acetate.

10. A method of diagnosing and treating metastatic bone lesions in a human comprising injecting an effective amount of the radiopharmaceutical claimed in claim 9 into said human.

11. The radioactive pharmaceutical claimed in claim 9 wherein said pharmaceutically acceptable eluent further comprises an antioxidant.

12. A method of diagnosing and treating metastatic bone lesions in a human comprising injecting an effective amount of the radiopharmaceutical claimed in claim 11 into said human.

13. The radioactive pharmaceutical claimed in claim 11 wherein said antioxidant is selected from the group consisting of ascorbic acid, gentisic acid and p-amino benzoic acid.

14. The radioactive pharmaceutical claimed in claim 11 wherein said pharmaceutically acceptable eluent further includes free ligand.

15. A method of diagnosing and treating metastatic bone lesions in a human comprising injecting an effective amount of the radiopharmaceutical claimed in claim 14 into said human.

* * * * *